United States Patent [19]

Miyawaki et al.

[11] Patent Number: 4,754,406
[45] Date of Patent: Jun. 28, 1988

[54] DEVICE FOR MEASURING BLOOD PRESSURE

[75] Inventors: Yoshinori Miyawaki, Yawata; Osamu Shirasaki, Amagasaki; Satoshi Ueno, Kyoto, all of Japan

[73] Assignee: Omron Tateisi Electronics Co., Kyoto, Japan

[21] Appl. No.: 711,417

[22] Filed: Mar. 13, 1985

[30] Foreign Application Priority Data

Mar. 13, 1984 [JP] Japan .................................. 59-48893
Mar. 14, 1984 [JP] Japan .................................. 59-49750

[51] Int. Cl.$^4$ .............................................. A61B 5/02
[52] U.S. Cl. ..................................... 364/416; 128/681
[58] Field of Search ................ 128/667, 672, 679-685; 364/416, 417

[56] References Cited

U.S. PATENT DOCUMENTS

| | | | |
|---|---|---|---|
| 3,903,872 | 9/1975 | Link | 128/681 |
| 4,009,709 | 3/1977 | Link et al. | 128/681 |
| 4,030,485 | 6/1977 | Warner | 128/667 |
| 4,074,711 | 2/1978 | Link et al. | 128/681 |
| 4,418,700 | 12/1983 | Warner | 128/672 X |
| 4,517,986 | 5/1985 | Bilgutay | 128/680 X |
| 4,543,962 | 10/1985 | Medero | 128/682 |
| 4,597,393 | 7/1986 | Yamakoshi et al. | 128/667 X |
| 4,625,277 | 11/1986 | Pearce | 364/416 |
| 4,664,126 | 5/1987 | Link | 128/680 |

OTHER PUBLICATIONS

"Blood Pressure by Oscillometry", Med. Electronics, Apr. 1978, J. Looney, Jr., pp. 57-63.

Primary Examiner—Joseph Ruggiero
Assistant Examiner—Charles B. Meyer
Attorney, Agent, or Firm—Wegner & Bretschneider

[57] ABSTRACT

An electronic device for measuring blood pressure, according to which either systolic pressure may be derived from mean pressure and diastolic pressure, or diastolic pressure may be derived from systolic pressure and mean pressure, whereby the time duration of the application of pressure to the patient's arm may be reduced because the pressure to be applied may only range substantially over between mean pressure and diastolic pressure or between systolic pressure and mean pressure. Additionally proposed is a means for improving the accuracy of the above-mentioned derivation of systolic pressure or diastolic pressure. As a result, considerable reduction in the time duration required for measurement may be reduced without any increase in measurement errors.

10 Claims, 8 Drawing Sheets

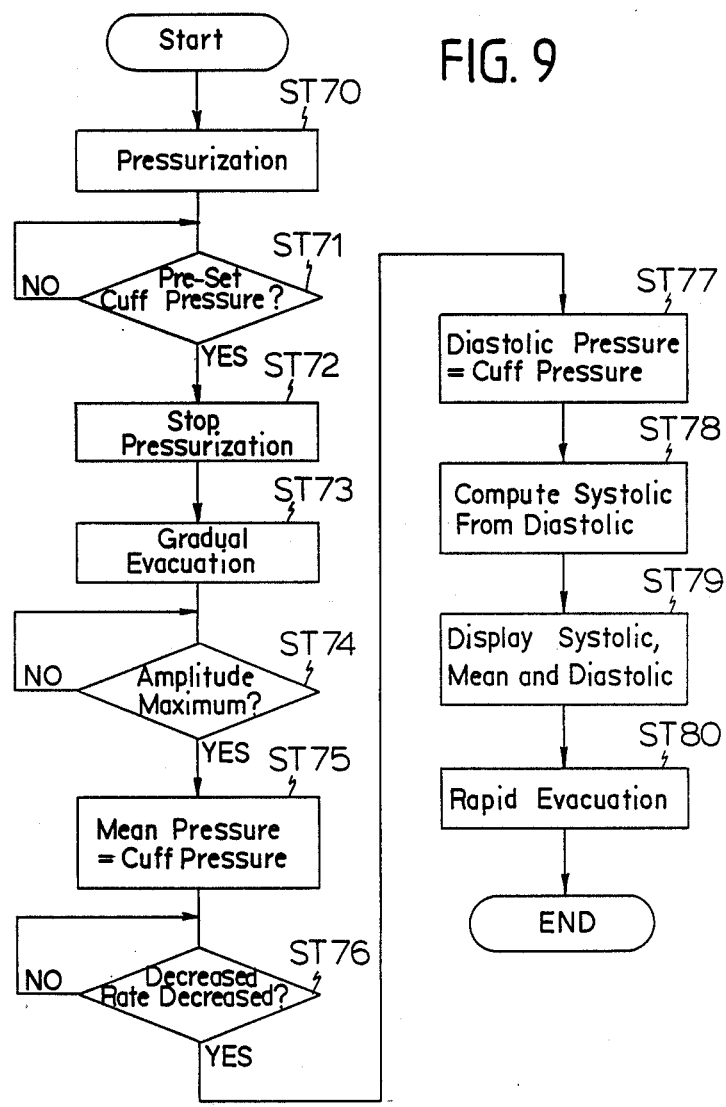

DEVICE FOR MEASURING BLOOD PRESSURE

BACKGROUND OF THE INVENTION

This invention relates to a device for measuring blood pressure and in particular to such a device which requires very a short time duration for measurement.

Generally, a device for measuring blood pressure, making use of a pressure cuff, is based on the processes of pressurizing a pressure cuff until the artery is completely closed, gradually evacuating the cuff (gradual evacuation) thereafter, and determining systolic pressure and /or diastolic pressure according to the detection of the Korotkoff sound (K sound) and its disappearance, or detecting pulsatile waves during the evacuation of the pressure cuff and obtaining the systolic pressure and /or the diastolic pressure from the point where rate of the increase and /or the decrease of the amplitude of the pulsatile wave increases and /or decreases, as the case may be.

Therefore, according to such devices for measuring blood pressure, the pressure cuff must be pressurized slightly over the systolic pressure (systolic pressure $+\alpha$) and subsequently evacuated until the pressure cuff pressure drops slightly below the diastolic pressure (diastolic pressure $-\beta$), and, therefore, the time duration required for measuring blood pressure was undesirably long. As a result, not only the time is wasted for measuring blood pressure, but also considerable pain was caused to the patient because of the pressure applied to his arm for a fairly long time duration, and it could even be hazardous for the patient if his physical condition is extremely grave. An additional disadvantage of the conventional devices was that possible congestion of blood may become a cause of measuring errors.

OBJECT OF THE INVENTION

In view of the problems mentioned above, a primary object of this inention is to provide a device for measuring blood pressure which requires a time duration for measurement which is substantially shorter than those required by conventional device for measuring blood pressure.

A second object of this invention is to provide a device for measuring blood pressure which is less painful to the patient than conventional ones.

A third object of this invention is to provide a device for measuring blood pressure which is accurate in spite of its high speed of measurement.

SUMMARY OF THE INVENTION

In order to achieve the above mentioned objects, according to a certain aspect of this invention, there is provided a device for measuring blood pressure according to the first invention of this application comprises: a pressure cuff; a pressurizing means for pressurizing the pressure cuff; an evacuation means for gradually or quickly evacuating the pressure cuff; a pressure sensor for detecting the pressure of the pressure cuff; a pulsatile wave detecting means for detecting pulsatile signals contained the pressure of the pressure cuff; a blood pressure determining means for determining systolic blood pressure and mean blood pressure from the wave form information of the pulsatile wave obtained by the pulsatile wave detecting means as the pressure cuff is being gradually evacuated by the evacuating means; and a diastolic pressure determining means for computing diastolic blood pressure from the systolic blood pressure and the mean blood pressure determined by the blood pressure determining means.

According to this device for measuring blood pressure, because the diastolic blood pressure is computed from the systolic blood pressure and the mean blood pressure, quick evacuation of the pressure cuff is possible immediately after the mean blood pressure is determined by a gradual evacuation of of the pressure cuff, and, therefore, the time duration required by the conventional devices between the determination of the mean blood pressure and the diastolic blood pressure may be omitted, whereby a considerable saving in the time required for the measurement can be accomplished.

According to another aspect of this invention, there is provided a device for measuring blood pressure comprising, in place of the said blood pressure determining means, a blood pressure determining means for determining mean blood pressure and diastolic blood pressure from the wave form information of the pulsatile wave obtained by the pulsatile wave detecting means as the pressure cuff is being gradually evacuated by the evacuating means; and, in place of the diastolic blood pressure determining means for computing systolic blood pressure from the mean blood pressure and the diastolic blood pressure determined by the blood pressure determining means.

According to this device for measuring blood pressure, because the systolic blood pressure is computed from the mean blood pressure and the diastolic blood pressure, the gradual evacuation may be started at a cuff pressure which is slightly higher than a predicted mean blood pressure and, therefore, the time durations, that were conventionally required for the pressurization of the pressure cuff and the gradual evacuation thereof for the determination of the systolic pressure, may be omitted, whereby a considerable saving in the time required for the measurement can be accomplished.

Because, according to either one of the first and the second aspects of this application, the time duration required for measurement is reduced and the time duration of applying pressure to an arm can be reduced, the pain to the patient can be reduced and an potential hazard to an emaciated or diathetic patients may be likewise diminished. Additionally, avoidance of any congestion of blood contributes to the elimination of measurement errors.

According to yet another aspect of this invention, there is provided a device for measuring blood pressure (electronic sphygmomanometer) according to which either systolic blood pressure and mean blood pressure are determined from the wave form information of a pulsatile wave signal and cuff pressure during the process of gradual evacuation of the pressure cuff and diastolic blood pressure is computed from (diastolic blood pressure)=(means blood pressure)-(1/A) (systolic blood pressure - mean blood pressure), or mean blood pressure and diastolic blood pressure are determined from the wave form information of a pulsatile wave signal and cuff pressure during the process of gradual evacuation of the pressure cuff and systolic blood pressure is computed from (systolic blood pressure)=(mean blood pressure)-A (mean blood pressure-diastolic blood pressure).

The constant A is to be set up in advance and A=2.0 is generally set up because it is appropriate in most cases. However, precisely speaking, the constant A may fluctuate from one person to another because of individual differences and fixing the constant A to a fixed value disregarding this fluctuation may lead to some measuring errors.

In view of such a problem, this invention further provides a devices for measuring blood pressure which is based on the steps of determining, in the first step, systolic blood pressure, mean blood pressure and diastolic blood pressure, computing a constant A from these blood pressure values, thereafter or in the second step, determining first the systolic blood pressure and the mean blood pressure or the mean blood pressure and the diastolic blood pressure according the the process of gradual evacuation of the pressure cuff, and then computing the remaining blood pressure value according to the constant A.

In other words, the device for measuring blood pressure according to this aspect of this invention, comprises: a pressure cuff; a pressurizing means for pressurizing the pressure cuff; an evacuation means for gradually or quickly evacuating the pressure cuff; a pressure sensor for detecting the pressure of the pressure cuff; a pulsatile wave detecting means for detecting pulsatile signals contained the pressure of the pressure cuff; a first blood pressure determining means for determining systolic blood pressure, mean blood pressure and diastolic blood pressure from the wave form information of the pulsatile wave obtained by the pulsatile wave detecting means as the pressure cuff is being gradually evacuated by the evacuating means; a constant value computing means for computing a constant value A=(-systolic blood pressure-mean blood pressure)/ (mean blood pressure-diastolic blood pressure) from the blood pressures determined by the first blood pressure determining means; a second blood pressure determining means for computing systolic blood pressure or diastolic blood pressure from the mean blood pressure and the diastolic blood pressure or the systolic blood pressure and the mean blood pressure determined by the blood pressure determining means during the gradual evacuation of the pressure cuff, and computing the systolic pressure or the diastolic blood pressure according to the constant value A which was computed by the constant value computing means; and a measurement control means which activates the first blood pressure determining means in a first stage and, in a intermittent and repetitive manner, activates the second blood pressure determining means in a second stage which follows the first stage.

According to this aspect of this invention, because, once the systolic blood pressure and the mean blood pressure or the mean blood pressure and the diastolic blood pressure are determined, the remaining systolic or diastolic blood pressure value can be readily computed, the measurement time may be reduced. And because the time duration of applying pressure to an arm can be reduced, the pain to the patient can be reduced and measurement errors may be reduced because of the absence of congestion of blood. Additionally, because the constant A computed from the patient at the particular time point is used for computing the remaining blood pressure value, fluctuations arising from individual difference and circumstantial difference may be compensated and a greater accuracy of measurement can be achieved.

BRIEF DESCRIPTION OF THE DRAWINGS

Now this invention is described with reference to the preferred embodiments thereof, and with reference to the illustrative drawings. It should be clearly understood, however, that the description of the embodiments, and the drawings are all of them given purely for the purpose of explanation and exemplification only, and are none of them intended to be limitative of the present invention in any way, since the scope of the present invention is to be defined solely by the legitimate and proper scope of the appended claims.

In the drawings, like parts and features are denoted by like reference numerals in the various figures thereof, and:

FIG. 3 (A) is a time chart of a cuff pressure, a pulsatile wave signal and a measuring time of the embodiment shown in FIGS. 1 to 3;

FIG. 3 (B) is a time chart of a cuff pressure, a pulsatile wave signal an a measuring time of a conventional electronic sphygmomanometer;

FIG. 9 is a flow chart of the routine of the measurement of mean blood pressure and diastolic blood pressure and the computation of systolic blood pressure in the main control flow of the same embodiment.

DESCRIPTION OF THE PREFERRED EMBODIMENTS

Figure 1:
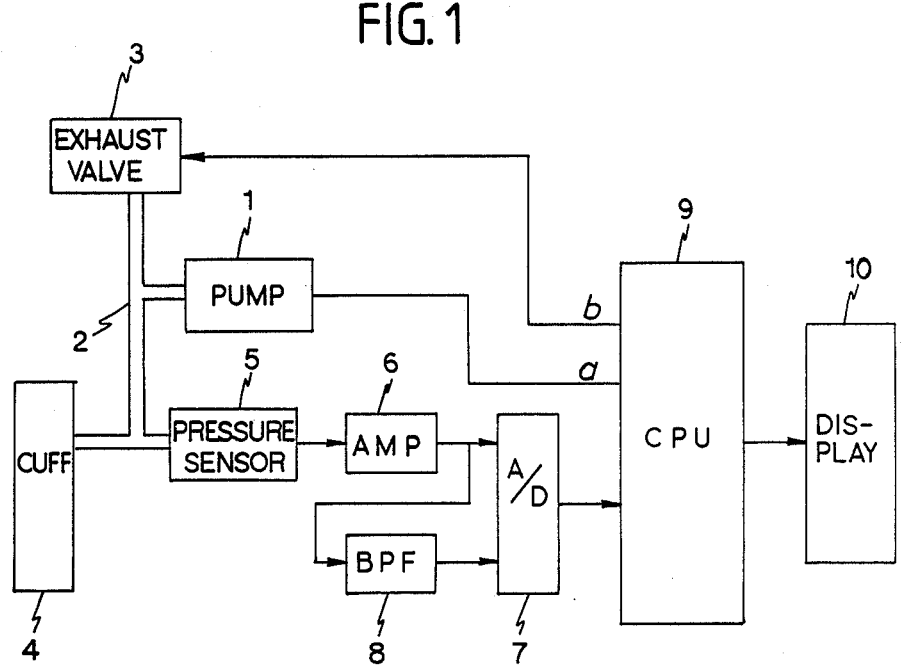
FIG. 1 is a block diagram of an embodiment of the electronic sphygmomanometer of this invention.

FIG. 1 is a block diagram of an electronic sphygmomanometer according to an embodiment of this invention. In this drawing, a pressurization pump 1 is communicated with an exhaust valve 3 and a pressure cuff 4 by way of an air conduit 2. The pressure cuff 4 is communicated with a pressure sensor 5 by way of another air conduit 2 so that the pressure in the pressure cuff 4 may be converted into an electric signal by the pressure sensor 5.

An output end of the pressure sensor 5 is connected to an amplifier 6, whose output end is connected to an input end of an A/D converter 7 and also to another input end of the A/D converter 7 by way of a band pass filter 8. Thus, one of the input ends of the A/D converter 7 is fed with a static pressure of the pressure cuff 4 from the amplifier 6 while the other of the input ends of the A/D converter 7 is fed with the pulsatile component of the pressure of the pressure cuff 4 from the band pass filter 8.

An output end of the A/D converter 7 is connected to a CPU 9 so that digitalized data of the cuff pressure and the pulsatile signal may be supplied to the CPU 9.

The CPU 9, which includes memory, such as RAM and ROM, therein, performs the functions of determining the systolic blood pressure and the means blood pressure and, based upon these blood pressure values, determining the diastolic blood pressure, according to a program stored in the ROM.

The CPU 9 additionally has control functions of driving and stopping at pressurization pump 1 according to a signal a and of switching over the exhaust valve 3 between a gradual evacuation and quick evacuation according to a signal b. The systolic blood pressure, the main blood pressure and the diastolic blood pressure, determined and computed by the CPU 9, are displayed by a display unit 10.

Figure 2:
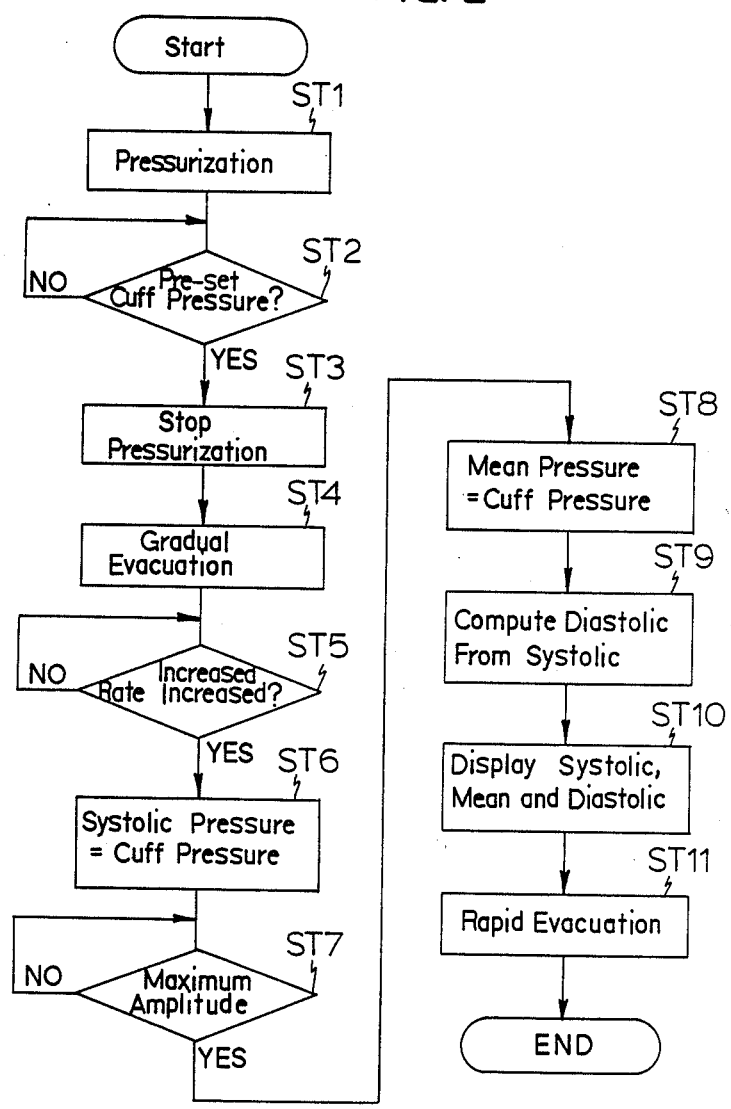
FIG. 2 is a control flow diagram of the embodiment of FIG. 1.

Although this sphygmomanometer is based on the oscillation method, according to which blood pressures are determined by making use of the amplitude of the pulsatile wave which is part of the wave form information of the pulsatile wave, a number of algorithms are known for determining the blood pressures according to the oscillation method, and, for instance, systolic and/or diastolic pressure may be determined as the cuff pressure corresponding to a certain fraction of the maximum value of the amplitude. In this embodiment, the following algorithm is used for the determination of the blood pressures:

- systolic blood pressure : cuff pressure when the increase rate of the amplitude of the pulsatile wave becomes great
- mean blood pressure : cuff pressure when the amplitude of the pulsatile wave takes the maximum value
- diastolic pressure : cuff pressure when the decrease rate of the amplitude of the pulsatile wave becomes small Now, the action of the sphygmomanometer of this embodiment is described in the following with reference to the flow chart given in FIG. 2.

As the action is started, the pressurizing pump 1 is driven by the signal a from the CPU 9 and the pressure cuff 4 is pressurized (step 1). Upon this pressurization, the cuff pressure abruptly rises as shown by a to b in FIG. 3 (A).

During this rise of the cuff pressure, it is determined as the cuff pressure is fed from the pressure sensor 5 into the CPU 9, whether the cuff pressure has reached a certain predetermined cuff pressure (which is generally higher than a predicted systolic blood pressure) or not (step 2). During the time the cuff pressure is lower than the predetermined value, the result of this determination is NO and the processing action remains at step 2. In the meantime, the pressurization by the pressurization pump 1 is continued.

When the cuff pressure reaches the predetermined value, the result of the determination process in step 2 turns into YES and the signal a is turned off, which terminates the driving the pressurization pump 1 and the pressurization of the pressure cuff 4 (step 3). At the same time, a gradual evacuation from the exhaust valve 3 is started and the cuff pressure begins declining, crossing over point b in FIG. 3 (A). The actual measurement is started at this time point. Specifically, it is determined whether the increasing rate of the amplitude of the pulsatile wave signal, fed from the band pass filter 8 into the CPU 9 by way of the A/D converter 7, is greater than a predetermined value or not, in step 5. If the amplitude of the pulsatile wave signal is substantially constant, the result of this determination is NO and the processing action remains at step 5. In the meantime, the cuff pressure gradually declines.

Figure 3:
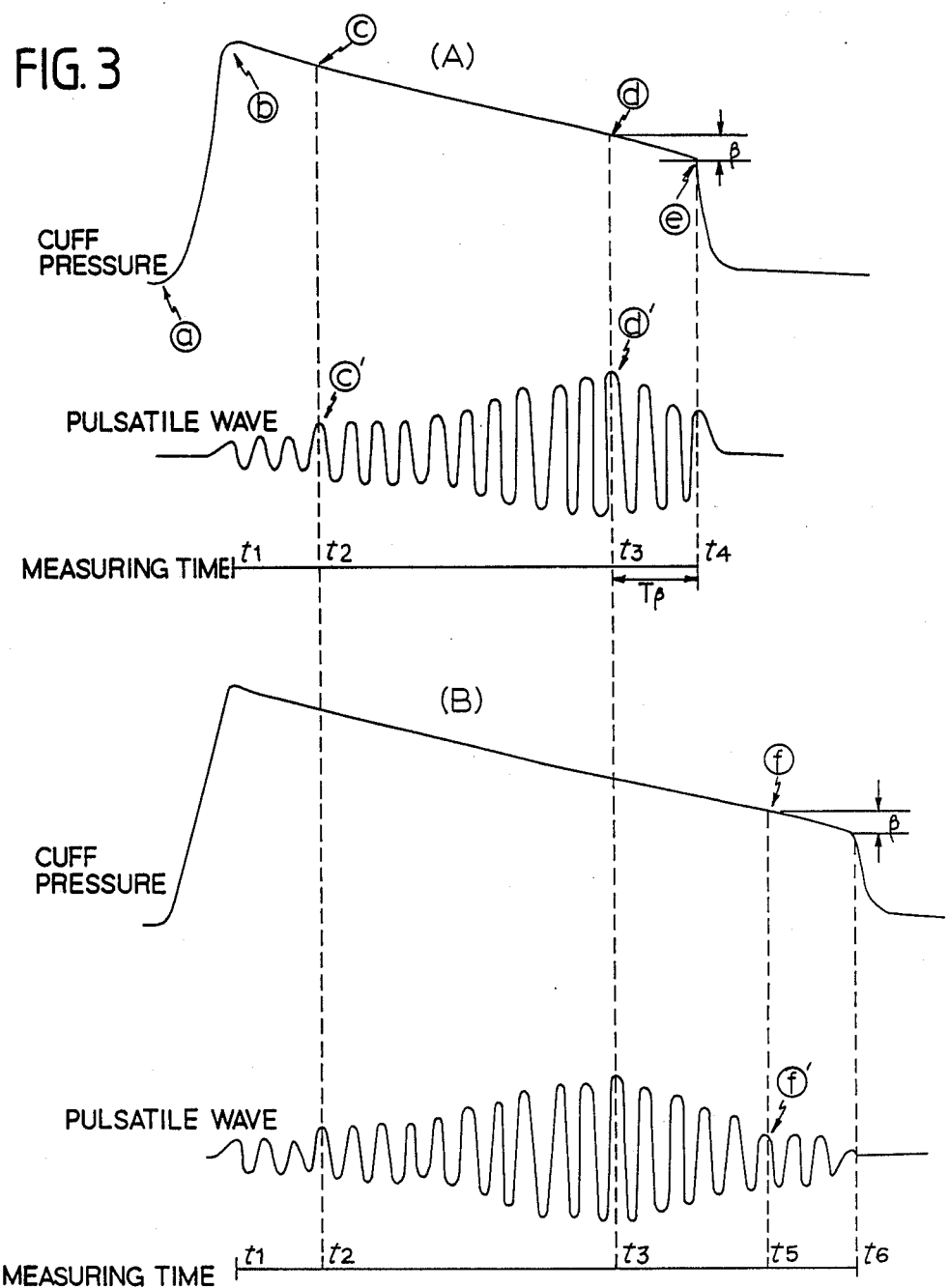
FIG. 3 is a time chart for showing the action and the advantages of the embodiment of FIG. 1 and 2.

When the increasing rate of the detected pulsatile wave signal exceeds the predetermined value (refer to point c' of FIG. 3 (A)), the determination result of step 5 turns into YES and the action flow proceeds to step 6. And the cuff pressure (refer to the point c in FIG. 3(A)) at this time point is determined as the systolic blood pressure. And this systolic blood pressure is stored in the memory of the CPU 9.

Even after the systolic blood pressure is determined, the cuff pressure continues declining through gradual evacuation of the pressure cuff. On the other hand, the amplitude of the pulsatile wave signal continues increasing. Therefore, in step 7, it is determined whether the amplitude of the pulsatile wave signal has reached the maximum value or not. As long as the amplitude of the pulsatile wave signal is rising, the determination result is NO and the processing action remains at step 7. However, when the amplitude of the pulsatile wave signal has reached the maximum value (refer to point d' in FIG. 3 (A)), the determination result turns into YES and the processing action proceeds to step 8. And the cuff pressure at this time point (refer to d in FIG. 3 (A)) is determined as the mean blood pressure. And this means blood pressure is likewise stored in the memory of the CPU 9.

Now that the systolic blood pressure and the mean blood pressure are determined, the diastolic blood pressure is computed from the systolic blood pressure and the mean blood pressure without waiting for the cuff pressure to be reduced to the level of a diastolic blood pressure (step 9).

The computation of the diastolic blood pressure is performed according to the following formula: (diastolic blood pressure)=(mean blood pressure)-systolic blood pressure-mean blood pressure)/A where the constant A is normally selected as 2.

Now that the systolic blood pressure and the mean blood pressure are determined and the diastolic blood pressure is computed, they are displayed on the display unit 10 (step 10).

Then the CPU 9 sends the signal b to the exhaust valve 3 so as to rapidly evacuate the pressure cuff 4 (step 11). However, because some time is required for selecting the maximum of the amplitude of the pulsatile wave signal, the rapid evacuation of the pressure cuff 4 takes place when the cuff pressure has dropped from the mean pressure by a value $\beta$ (refer to the point e in FIG. 3 (A)). There is, therefore, a slight delay $T_\beta$ in the onset of the rapid evacuation of the pressure cuff 4. As a result, the total time duration required for measurement with the electronic sphygmomanometer of this embodiment corresponds to the duration from $t_1$ to $t_4$ as shown in FIG. 3 (A).

FIG. 3 (B) is a time chart of a cuff pressure, a pulsatile signal and a measurement time according to a conventional electronic sphygmomanometer, and is given here for comparison with FIG. 3 (A). According to this conventional electronic sphygmomanometer, the diastolic pressure is also determined from the amplitude of the pulsatile wave signal. In other words, the cuff pressure corresponding to the point f' at which the decreasing rate of the amplitude diminishes is determined as the diastolic blood pressure (refer for the point f in FIG. 3 (A)). Therefore, the time required for measurement in this case is from $t_1$ to $t_6$. It can be readily seen by comparing the time durations required for measurement in FIG. 3 (A) and 3 (B), the one given in FIG. 3 (A) is shorter than the other.

Now another embodiment of the electronic sphygmomanometer according this invention is described in the following.

The circuit structure of this embodiment is identical to the one shown in FIG. 1 but the processing action in its CPU 9 proceeds in a different manner.

According to the electronic sphygmomanometer, whose flow chart is shown in FIG. 1, the cuff pressure is decreased from a level which is higher than that of systolic blood pressure, and the amplitude of the pulsatile wave signal is detected. Based on the detected amplitude of the pusatile wave signal, the systolic blood pressure and the mean blood pressure are determined, and the diastolic blood pressure is computed from the systolic blood pressure and the mean blood pressure thus determined, before the rapid evacuation of the pressure cuff takes place. Therefore, according to this electronic sphygmomanometer, the cuff pressure is selected at a level which is slightly higher than the mean blood pressure and the gradual evacuation of the pressure cuff is started from this point so that the mean pressure and then the diastolic blood pressure may be determined from the amplitude of the pulsatile wave signal and the systolic blood pressure may be computed from the mean blood pressure and the diastolic blood pressure, before the rapid evacuation of the pressure cuff. The two embodiments are common in reducing the time duration required for measurement, but the second embodiment can reduce the time duration even more, according to its working principle, because the time duration between the time $t_3$ of detecting the mean blood pressure and the time $t_5$ of detecting the diastolic blood pressure is normally shorter than the time duration between the time $t_2$ of detecting the systolic blood pressure and the time $t_3$ of detecting the mean blood pressure, as shown in FIG. 3 (B).

Figure 4:
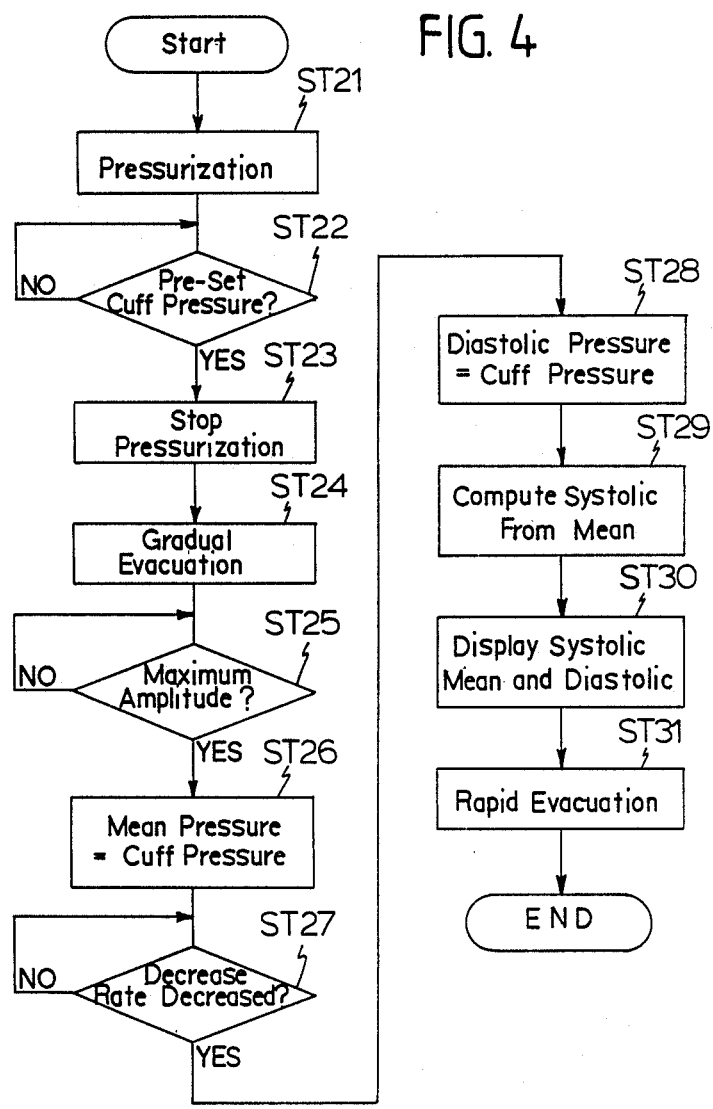
FIG. 4 is a control flow diagram of a second embodiment of the electronic sphygmomanometer of this invention.

FIG. 4 is a control flow diagram of the second embodiment of the electronic sphygmomanometer of this invention. In this flow diagram, the processing action from step 21 to step 24 is substantially identical to that from step 1 to step 4 shown in FIG. 2. However, a difference exists in that the predetermined value in step 22 is selected so that (mean blood pressure)<(predetermined value)<(systolic blood pressure).

When a gradual evacuation is started in step 24, first, the maximum amplitude of the pulsatile wave signal is determined (step 25) and, upon detection of the maximum value, the cuff pressure at the time is determined as the mean blood pressure (step 26). During the succeeding gradual evacuation of the cuff pressure, the point at which the decreasing rate of the amplitude of the pulsatile wave signal diminishes is determined (step 27) and this cuff pressure is determined as the diastolic blood pressure (step 28). Then, the systolic blood pressure is computed from the determined mean blood pressure and diastolic blood pressure (step 29). The computation of the systolic blood pressure is performed according to the following formula: (systolic blood pressure)=(mean blood pressure)+A (mean blood pressure−diastolic blood pressure). Then, in a similar way as that shown in FIG. 2, the systolic blood pressure, the mean blood pressure and the diastolic blood pressure, thus determined and computed, are displayed on the display unit 10 (step 50), followed by rapid evacuation of the pressure cuff 4 (step 51).

Although, in the above described embodiments, the pressurization and evacuation of the pressure cuff are automatically performed by the control from the CPU 9, this invention is not limited thereby, but may also be applied to the case of manual pressurization and manual evacuation of the pressure cuff. If manual evacuation is to be adopted, it is desirable to show, for instance by a buzzer, the beginning of a rapid evacuation.

Figure 5:
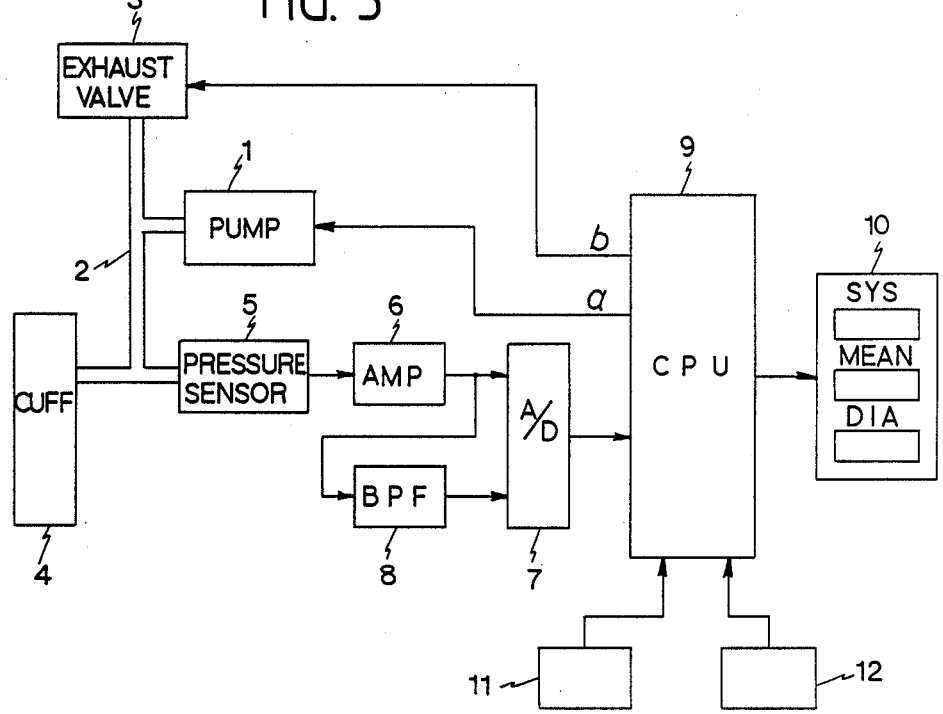
FIG. 5 is a block diagram of an embodiment of the electronic sphygmomanometer of this invention.

FIG. 5 is a block diagram of an electronic sphygmomanometer according to a third embodiment of this invention. The structure of this embodiment is very similar to the one shown in FIG. 1, in connection with the first and the second embodiments, but a pair of digital switches 11 and 12 are connected to the CPU 9 and their functions will be described later.

The CPU 9, which includes memory, such as RAM and ROM, therein, performs the functions of determining the systolic blood pressure, the means blood pressure and the diastolic blood pressure, computing a constant A from these blood pressure value according to A=(systolic blood pressure−mean blood pressure)/(mean blood pressure−diastolic blood pressure), and computing the systolic blood pressure from the computed constant A and the newly determined mean blood pressure and diastolic blood pressure, according to a program stored in the ROM.

The CPU 9 further has a T1 timer and a T2 timer internally. The time durations to be set up in these timers are set up by digital switches 11 and 12. These time durations are selected so that $T1 < < T2$.

Figure 6:
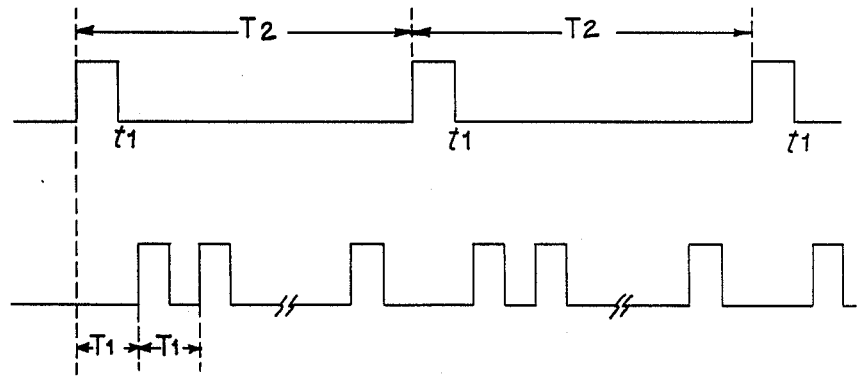
FIG. 6 is a timing chart of the timers provided in the above sphygmomanometer.

The electronic sphygmomanometer of this embodiment first determines systolic blood pressure, mean blood pressure and diastolic pressure through a series of cuff pressure variations of pressurization, gradual evacuation and rapid evacuation of the pressure cuff, and computes a the constant A from these blood pressure values (the constant A is computed at t1 in FIG. 6).

Thereafter, the processes of pressurization, gradual evacuation, rapid evacuation and intermission are repeated at a duration of T1, and the systolic pressure is computed from the determined mean blood pressure, diastolic blood pressure and constant A. The obtained blood pressure values are displayed on a display 10.

Although this sphygmomanometer is based on the oscillation method, according to which blood pressures are determined by making use of the amplitude of the pulsatile wave which is part of the wave form information of the pulsatile wave, a number of algorithms are known for determining the blood pressures according to the oscillation method, but, in this embodiment, the following algorithm is used for the determination of the blood pressures:

systolic blood pressure : cuff pressure when the increase rate of the amplitude of the pulsatile wave becomes great
  mean blood pressure : cuff pressure when the amplitude of the pulsatile wave takes the maximum value
  diastolic pressure : cuff pressure when the decrease rate of the amplitude of the pulsatile wave becomes small Now, the action of the sphygmomanometer of this embodimennt is described in the following with reference to the flow charts given in FIGS. 7, 8 and 9.

As the action is started, the T1 time is started (step 41), and the T2 time is simultaneously started (step 42).

And systolic blood pressure, mean blood pressure and diastolic blood pressure are determined (measured) and the constant A is computed (step 43).

Figure 8:
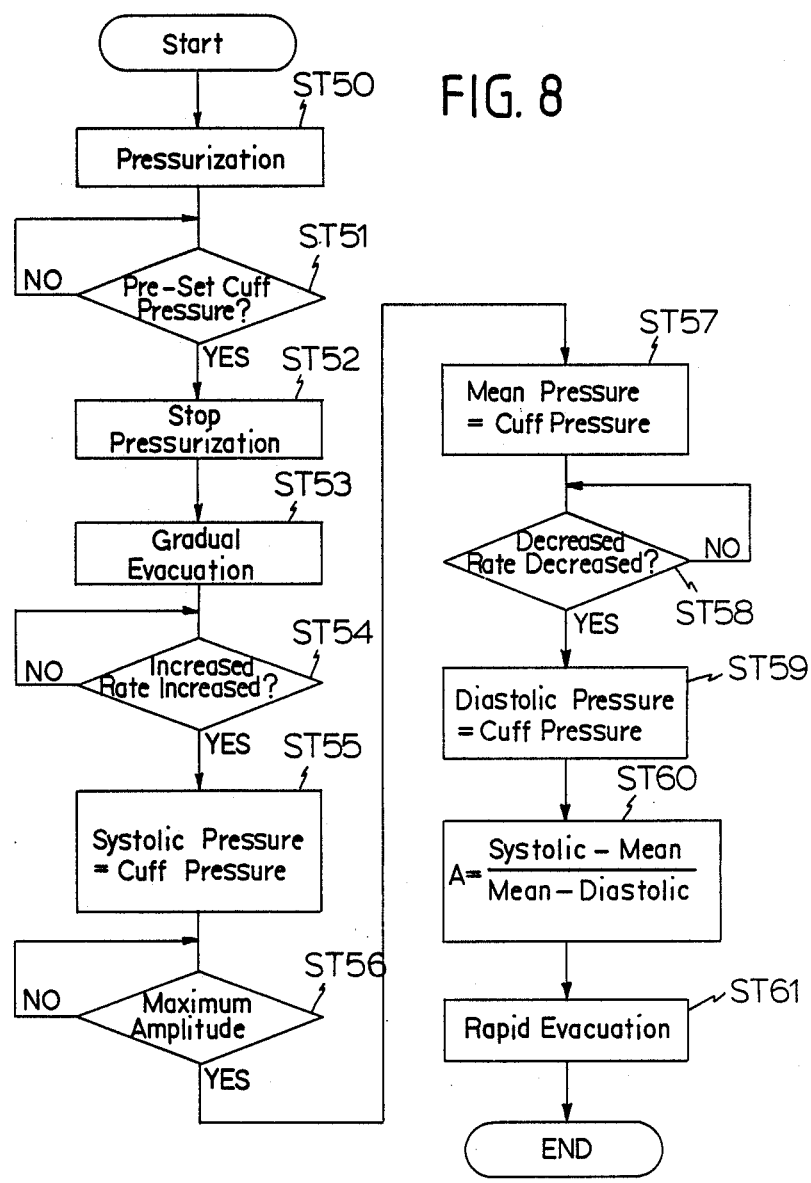
FIG. 8 is a flow chart of the constant comprising routine in the main control flow of the same embodiment.

The processes of the determination of the blood pressures and the constant A are shown in detail in FIG. 8. In other words, in this routine, the pressurizing pump 1 is driven by the signal a from the CPU 9 and the pressure cuff 4 is pressurized (step 50). Upon this pressurization, the cuff pressure abruptly rises.

During this rise of the cuff pressure, it is determined, for each sample time, as the cuff pressure is fed from the pressure sensor 5 into the CPU 9, whether the cuff pressure has reached a certain predetermined cuff pressure (which is generally higher than a predicted systolic blood pressure) or not (step 51). During the time the cuff pressure is lower than the predetermined value, the result of this determination is NO and the processing action remains at step 51. In the meantime, the pressurization by the pressurization pump 1 is continued.

When the cuff pressure reaches the predetermined value, the result of the determination process in step 51 turns into YES and the signal a is turned off, which terminates the driving of the pressurization pump 1 and the pressurization of the pressure cuff 4 (step 52). At the same time, a gradual evacuation from the exhaust valve 3 is started and the cuff pressure begins declining (step 53).

Thereafter, it is determined whether the increase rate of the amplitude of the pulsatile wave signal supplied to the CPU 9 has exceeded a certain value or not (step 54). If the increase rate of the amplitude of the pulsatile wave is substantially constant, then the determination result is NO and the process action remains at this step. In the meantime, the cuff pressure gradually declines.

When the increasing rate of the detected pulsatile wave signal exceeds the predetermined value, the determination result of step 54 turns into YES and the cuff pressure at this point is determined as systolic blood pressure. This systolic blood pressure is stored in the memory of the CPU 9 (step 55).

Even after the systolic blood pressure is determined, the cuff pressure continues declining through gradual evacuation of the pressure cuff. On the other hand, the amplitude of the pulsatile wave signal continues increasing. Therefore, in step 56, it is determined whether the amplitude of the pulsatile wave signal has reached the maximum value or not. As long as the amplitude of the pulsatile wave signal is rising, the determination result is NO and the processing action remains at step 56. However, when the amplitude of the pulsatile wave signal has reached the maximum value, the determination result turns into YES and the cuff pressure at this time point is determined as mean blood pressure. And this mean blood pressure is likewise stored in the memory of the CPU 9 (step 57).

Even after the mean blood pressure is determined, the cuff pressure continues declining through gradual evacuation of the pressure cuff. And, the amplitude of the pulsatile wave signal likewise decreases. Then it is determined whether the decrease rate of the pulsatile wave signal is smaller that a certain predetermined value or not (step 58). If the amplitude of the pulsatile wave signal is declining, the determination result is NO and the process flow remains at step 58, but, if the amplitude of the pulsatile wave signal is constant or the decrease rate of the amplitude of the pulsatile wave signal has become less than the predetermined value, then the determination result is YES and the cuff pressure at this time point is determined as diastolic blood pressure (step 59). This diastolic pressure is also stored in the memory of the CPU 9.

Thus the systolic blood pressure, the mean blood pressure and the diastolic pressure are determined. However, the method of determining blood pressure was the same as that in a conventional electronic sphygmomanometer.

Then the computation of A=(systolic blood pressure-mean blood pressure)/(mean blood pressure-diastolic blood pressure) is performed and the constant A is computed and stored in the memory (step 60). Then, the CPU 9 supplies the signal b to the exhaust valve 3 and switches it over to rapid evacuation, and the pressure of the pressure cuff 4 is rapidly decreased (step 61).

Figure 7:
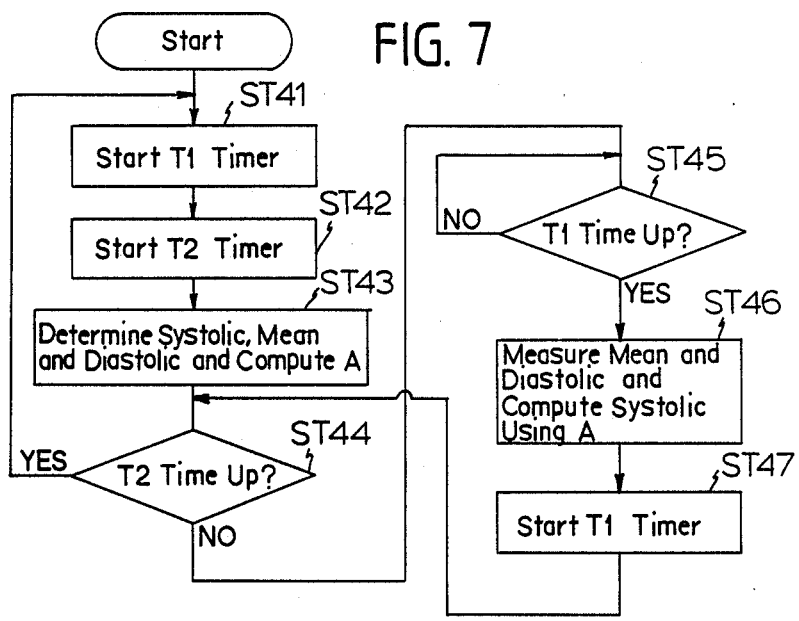
FIG. 7 is a control flow diagram of the embodiment of FIG. 5.

Upon completion of this process, the process flow escapes from step 44 of FIG. 7 and moves over to step 45 for the determination whether the T2 timer is up or not. This determination result is initially NO and, after the process flow has advanced to step 45, it is determined whether the T1 time is up or not and this continues until the T1 timer times up. In the meanwhile, the measurement of blood pressure is suspended. In other words, an intermission of measurement takes place and continues until the next measurement is made.

When the T1 timer times up, then the determination result in step 45 turns into YES, mean blood pressure and diastolic blod pressure are determined (measured) in step 46, and systolic blood pressure is determined from these mean blood pressure and diastolic blood pressure and the already computed constant A.

The routine of the determination of mean blood pressure and diastolic blood pressure and computation of systolic blood pressure in step 46 is shown in detail in FIG. 9.

Upon entry into this routine, the pressure cuff 4 is pressurized (step 70), it is determined whether the cuff pressure has reached a predetermined value (step 71) and, when it has reached the predetermined value, the pressurization is terminated (step 72) and gradual evacuation of the pressure cuff 4 begins (step 73). The process flow so far is similar to steps 50 to 53 to the routine shown in FIG. 8. But a difference exists in that the predetermined value of step 71 is set up at a value which is slightly greater than the mean blood pressure.

When a gradual evacuation is started in step 73, first, the maximum amplitude of the pulsatile wave signal is determined (step 74) and, upon detection of the maximum value, the cuff pressure at the time is determined as the mean blood pressure (step 75). During the succeeding gradual evacuation of the cuff pressure, the point at which the decreasing rate of the amplitude of the pulsatile wave signal diminishes is determined (step 76) and this cuff pressure is determined as the diastolic blood pressure (step 77). Then, the systolic blood pressure is computed from the determined mean blood pressure and diastolic blood pressure (step 78). The computation of the systolic blood pressure is performed according to the following formula: (systolic blood pressure)=(mean blood pressure)+A (mean blood pressure-diastolic blood pressure). Here the constant A is the one which has already been computed and stored in memory. Then, the systolic blood pressure, the mean blood pressure and the diastolic blood pressure, thus determined and computed, are displayed on the display unit 10 (step 79). And upon completion of the measurement, rapid evacuation is selected (step 80) and the pressure cuff 4 is rapidly evacuated.

Upon completion of this process, the process flow escapes from step 46 of FIG. 7 and, after the T1 timer is started in step 47, returns to step 44. And the processes from step 45 to step 47 are repeated until the T2 timer runs out. In other words, the measurement based on the process flow shown in FIG. 9 is repeated.

Because this measurement is based on pressurization of the pressure cuff to a pressure value which is slightly higher than the mean blood pressure, gradually evacuating it until the diastolic blood pressure is determined and, thereafter, rapidly evacuating it, the time duration of pressurization may be drastically reduced.

Figure 10:
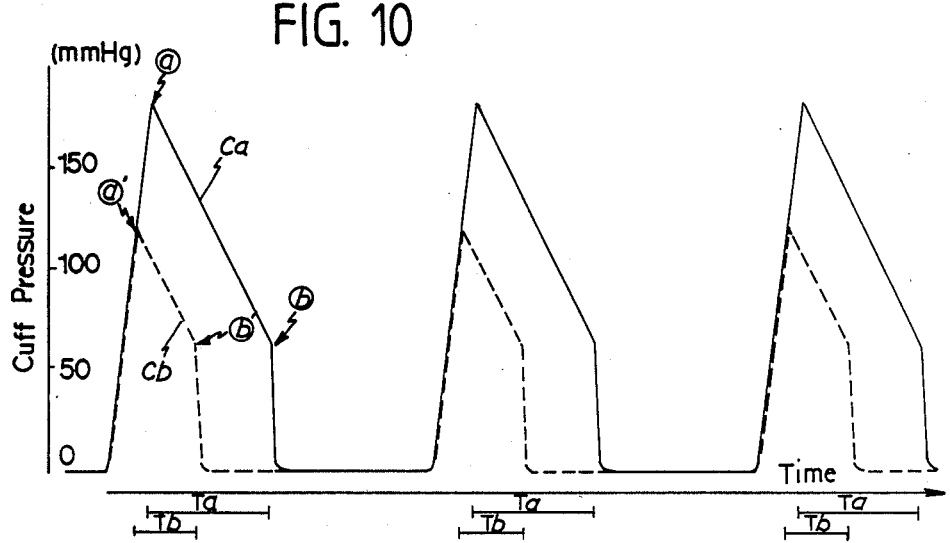
FIG. 10 is a diagram showing the cuff pressure change in continuous measurements made with the electronic sphygmomanometer of this embodiment and a conventional electronic sphygmomanometer.

FIG. 10 shows how this is performed. FIG. 10 shows the change in the cuff pressure when a measurement was continuously conducted on a person with systolic blood pressure of 160 mmHg, mean blood pressure of 100 mmHg and diastolic blood pressure of 70 mmHg. In this graph, the cuff pressure changes indicated by the solid line Ca are a result of a continuous measurement with a conventional electronic sphygmomanometer while the cuff pressure changes indicated by the broken line Cb is a result of a continuous measurement with the electronic sphygmomanometer of this emboidment. Because the pressure cuff 4 is pressurized up to a point (point a') which is slightly above the mean blood pressure and is gradually evacuated down to a point (point b') which is slightly below the diastolic blood pressure according to this electronic sphygmomanometer, while, according to the conventional one, the pressure cuff is pressurized up to a point (point a) which is higher than the systolic blood pressure and gradually evacuated down to a point (point b) which is lower than the diastolic blood pressure, the measurement time duration is thus drastically reduced to Tb, as opposed to the time duration Ta.

When the T2 timer runs out, the determination result in step 44 turns into YES and the process flow returns to step 41, where the constant A is computed again (steps 41 to 43). In other words, the constant A is updated. By proper selection of the setting of the T2 timer, it is possible to update the constant A at an arbitrary frequency and therefore it becomes possible to increase the accuracy of the measurement because the systolic blood pressure may be computed with the influences from the individual differences of the patient and the circumstantial conditions properly compensated even if such influences are present.

Although, in the above embodiment, the constant A and the systolic pressure were computed after the mean blood pressure and the diastolic blood pressure are determined through repetitive and intermittent measurements, it is also possible to compute the diastolic blood pressure from the formula: (diastolic blood pressure)=(mean blood pressure)-(1/A)(systolic blood pressure-mean blood pressure).

Furthermore, the constant A was updated after each time duration of T2 which is set on the T2 timer, but it is also possible to provide a special function key so that the measurement process of computing the constant A may be performed only when the key is pressed.

Although the present invention has been shown and described in terms of the preferred embodiments thereof, and with reference to the illustrative drawings, it should not be considered as limited thereby. Various possible modifications and alterations could be conceived of by one skilled in the art to any particular embodiment, without departing from the scope of the invention.

Therefore it is desired that the scope of the invention should be defined not by any of the perhaps purely fortuitous details of the shown preferred embodiments, or of the drawings, but solely by the scope of the appended claims, which follows.

What is claimed is:

1. A device for measuring blood pressure comprising:
a pressure cuff;
a pressurizing means for pressurizing the pressure cuff;
an evacuation means for gradually or quickly evacuating the pressure cuff;
a control means for automatically controlling said pressurizing and said evacuating of said pressure cuff;
a pressure sensor for detecting the pressure of the pressure cuff;
a pulsatile wave detecting means for detecting pulsatile signals contained in the pressure of the pressure cuff;
a blood pressure determining means for determing systolic blood pressure and mean blood pressure from the wave form information of the pulsatile wave obtained by the pulsatile wave detecting means as the pressure cuff is being gradually evacuated by the evacuating means; and
diastolic pressure determining means for computing diastolic blood pressure from the systolic blood pressure and the mean blood pressure determined by the blood pressure determining means.

2. A device for measuring blood pressure as defined in claim 1, wherein the computation at the diastolic pressure determining means is performed according to a formula: (diastolic blood pressure)=(mean blood pressure)-(1/A) (systolic blood pressure-mean blood pressure) where A is a constant.

3. A device for measuring blood pressure as defined in claim 2, wherein the constant A is substantially equal to 2.0.

4. A device for measuring blood pressure as defined in claim 2, wherein the constant A is substantially equal to 2.0.

5. A device for measuring blood pressure as defined in claim 1, further comprising a band pass filter connected between the pressure sensor and the blood pressure determining means, for providing the pulsatile component of the pressure contained in the pressure of the pressure cuff.

6. A device for measuring blood pressure, comprising:
a pressure cuff;
a pressurizing means for pressurizing the pressure cuff;
an evacuation means for gradually or quickly evacuating the pressure cuff;
a control means for automatically controlling said pressurizing and said evacuating of said pressure cuff;
a pressure sensor for detecting the pressure of the pressure cuff;
a pulsatile wave detecting means for detecting pulsatile signals contained in the pressure of the pressure cuff;
a blook pressure determining means for determining mean blood pressure and diastolic blood pressure from the wave form information of the pulstile wave obtained by the pulsatile wave detecting means as the pressure cuff is being gradually evacuated by the evacuating means; and a systolic pressure determining means for computing systolic blood pressure from the mean blood pressure and the diastolic blood pressure determined by the blood pressure determining means.

7. A device for measuring blood pressure as defined in claim 6, wherein the computation at the systolic pressure determining means is performed according to a formula: (systolic blood pressure)=(mean blood pressure)-A (mean blood presure-diastolic blood pressure) where A is a constant.

8. A device for measuring blood pressure as defined in claim 7, wherein the constant A is substantially equal to 2.0.

9. A device for measuring blood pressure as defined in claim 7, wherein the constant A is substantially equal to 2.0.

10. A device for measuring blood pressure, comprising:

a pressure cuff; a pressurizing means for pressurizing the pressure cuff; an evacuation means for gradually or quickly evacuating the pressure cuff; a pressure sensor for detecting the pressure of the pressure cuff; a pulsatile wave detecting means for detecting pulsatile signals continued in the pressure of the pressure cuff; a first blood pressure determining means for determining systolic blood pressure, mean blood pressure and diastolic blood pressure from the wave form information of the pulsatile wave obtained by the pulsatile wave detecting means as the pressure cuff is being gradually evacuated by the evacuating means; a constant value computing means for computing a constant value A=(systolic blood pressure-mean blood pressure)/(mean blood pressure-diastolic blood pressure) from the blood pressures determined by the first blood pressure determining means; a second blood pressure determining means for computing systolic blood pressure or diastolic blood pressure from the mean blood pressure and the diastolic blood pressure or the systolic blood pressure and the mean blood pressure determined by the first blood pressure determining means during the gradual evacuation of the pressure cuff, and computing the systolic pressure or the diastolic blood pressure according to the constant value A which was computed by the constant value computing means; and a measurement control means which activates the first blood pressure determining means in a first stage and, in an intermittent and repetitive manner, activates the second blood pressure determining means in a second stage which follows the first stage.

* * * * *